United States Patent
Reynolds et al.

(10) Patent No.: US 7,645,283 B2
(45) Date of Patent: *Jan. 12, 2010

(54) RETRIEVAL BASKET WITH RELEASABLE TIP

(75) Inventors: Robert Reynolds, Northboro, MA (US); M. Kevin Richardson, Hopkinton, MA (US); Mark Bowen, Stow, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 989 days.

This patent is subject to a terminal disclaimer.

(21) Appl. No.: 10/720,598

(22) Filed: Nov. 24, 2003

(65) Prior Publication Data

US 2004/0116941 A1 Jun. 17, 2004

Related U.S. Application Data (63) Continuation of application No. 10/040,720, filed on Jan. 7, 2002, now Pat. No. 6,673,080.

(60) Provisional application No. 60/260,299, filed on Jan. 8, 2001.

(51) Int. Cl.
*A61B 17/24* (2006.01)

(52) U.S. Cl. .................................................. 606/113

(58) Field of Classification Search ..... 606/127–128 M, 606/113, 110, 114, 159, 200
See application file for complete search history.

(56) References Cited

U.S. PATENT DOCUMENTS

| | | | | |
|---|---|---|---|---|
| 4,467,930 A | * | 8/1984 | Schnell et al. | 215/48 |
| 4,590,938 A | | 5/1986 | Segura et al. | 606/127 |
| 5,059,199 A | * | 10/1991 | Okada et al. | 606/127 |
| 5,176,688 A | | 1/1993 | Narayan et al. | 606/128 |
| 5,374,273 A | | 12/1994 | Nakao et al. | 606/127 |
| 5,462,553 A | * | 10/1995 | Dolgin | 606/113 |
| 5,792,145 A | * | 8/1998 | Bates et al. | 606/127 |
| 5,935,139 A | * | 8/1999 | Bates | 606/159 |
| 5,944,728 A | * | 8/1999 | Bates | 606/127 |
| 5,957,932 A | | 9/1999 | Bates et al. | 606/127 |
| 6,059,793 A | | 5/2000 | Pagedas | 606/114 |

(Continued)

FOREIGN PATENT DOCUMENTS

WO WO 93/15671 8/1993

(Continued)

OTHER PUBLICATIONS

International Search Report for International Patent Application No. PCT/US02/00383, dated Sep. 12, 2002, 9 pages.

*Primary Examiner*—Cris L Rodriguez
*Assistant Examiner*—Heidi M Eide
(74) *Attorney, Agent, or Firm*—Crompton, Seager & Tufte, LLC (57) ABSTRACT

A medical retrieval device is used to retrieve and/or fragment stones (and/or other objects) from the body of a patient. The device has a retrieval basket with a releasable tip. The tip release is designed to release in a controlled pre-determined manner and under a pre-determined force before any other component of the device fails due to a force exerted on the basket.

21 Claims, 5 Drawing Sheets

U.S. PATENT DOCUMENTS

| | | | | |
|---|---|---|---|---|
| 6,077,274 A * | 6/2000 | Ouchi et al. | | 606/113 |
| 6,083,220 A | 7/2000 | Guglielmi et al. | | 606/32 |
| 6,096,053 A | 8/2000 | Bates | | 606/159 |
| 6,152,932 A | 11/2000 | Ternström | | 606/114 |
| 6,159,220 A | 12/2000 | Gobron et al. | | 606/127 |
| 6,187,017 B1 | 2/2001 | Gregory, Jr. | | 606/127 |
| 6,224,612 B1 | 5/2001 | Bates et al. | | 606/114 |
| 6,264,664 B1 | 7/2001 | Avellanet | | 606/128 |
| 6,319,262 B1 | 11/2001 | Bates et al. | | 606/127 |
| 6,605,102 B1 * | 8/2003 | Mazzocchi et al. | | 606/200 |
| 6,800,080 B1 * | 10/2004 | Bates | | 606/127 |
| 6,872,211 B2 * | 3/2005 | White et al. | | 606/114 |

FOREIGN PATENT DOCUMENTS

| | | |
|---|---|---|
| WO | WO 99/48429 | 12/1999 |
| WO | 00/71036 A2 | 11/2000 |
| WO | 01/10290 A2 | 2/2001 |

\* cited by examiner

RETRIEVAL BASKET WITH RELEASABLE TIP

CROSS-REFERENCE TO RELATED APPLICATIONS

This application is a continuation of U.S. patent application Ser. No. 10/040,720, filed on Jan. 7, 2002 now U.S. Pat. No. 6,673,080, which claims priority to and the benefit of U.S. provisional patent application Ser. No. 60/260,299, filed on Jan. 8, 2001, the disclosures of which are incorporated herein by reference in its entirety.

TECHNICAL FIELD

The present invention generally relates to medical retrieval devices for capturing material such as stones within a body and to medical retrieval devices featuring a basket which captures one or more stones located in a body tract and which optionally fragments, crushes, or releases the stones.

BACKGROUND OF THE INVENTION

Medical retrieval devices for capturing stones in a body tract generally include a basket. Some medical retrieval baskets are also mechanical lithotriptors which optionally crush or fragment stones that are too large to be removed intact from the body tract after the stone has been captured within the basket. One type of known device for crushing or breaking stones in a body tract has a wire basket that is typically introduced into a body tract via a working channel of an endoscope or by means of a guidewire.

Baskets designed for mechanical retrieval are typically constructed from a plurality of wires that are arranged and shaped such that their natural form, when unrestrained, is to expand radially outward. The basket wires are gathered together at their distal ends and at their proximal ends to form a basket. An elongated traction member typically extends from the basket through a sheath to a handle.

A typical retrieval basket is introduced into a body tract via an endoscope or catheter and maneuvered around the stone until the stone enters the basket. If it is necessary to reduce the size of the stone, it is then fragmented typically by applying tension to the basket wires surrounding the stone until sufficient force is applied directly to the stones by the basket wires to cause the stone to break apart.

Mechanical limitations and wide variation in the size, location, shape, and composition of stones in the body present problems in retrieving stones in a body tract. Methods that are used to reduce the size of the stone include lithotripsy such as by acoustic shock waves delivered to the stone from within or outside the body, laser energy applied directly to the stone, or compressive force applied to the stone by means of a mechanical basket. If mechanical basket lithotripsy is attempted on a stone composed of very hard material, the basket wire tension required to fragment the stone may exceed the strength of the basket wires, the various connecting joints of the medical device, the elongated traction member attached to the basket base, or the sheath. If the path of the body tract is very tortuous, the bends in the body tract will cause intimate contact of the traction member with the interior surface of the sheath. The friction generated between the traction member and the sheath will cause the tension applied to the proximal end of the traction member to be greatly reduced when delivered to the basket wires. It is possible for the mechanical strength of the basket wires, the various connecting joints in the device, the traction member, or the sheath to be exceeded even when fragmenting stones of only moderately hard composition.

Failure of the medical retrieval device, including the retrieval basket or any of its components, following capture of a stone may require release of the stone before the basket can be withdrawn from the body tract. Failure of a medical device may occur, for example, near the proximal end of a traction member impairing the ability of the operator to manipulate the basket from the proximal end of the device to remove the basket and captured stone from the body tract. Alternatively, the traction member may fail at the distal end of the device. The broken end of the traction member may traumatize the lining of the body tract if an attempt is made to withdraw the failed device from the body tract. If one or more of the basket wires fail, it may be impossible to remove the basket via the same route by which the basket was introduced into the body tract without traumatizing the lining of the body tract with the fragmented ends of the broken basket wires.

With most known retrieval baskets, it is difficult to disengage the stone from the basket so that the basket can be removed from the body tract. Retrieval baskets typically lack sufficient strength to break the stone. Attempts to perform lithotripsy may result in failure of the device, including failure of the retrievable basket or any of its components. If the stone can not be released from the basket, more invasive surgical approaches are required to disengage the stone from the basket and to remove the basket and stone from the body tract.

SUMMARY OF THE INVENTION

It is an object of the invention to provide a medical device useful for retrieval of one or more stones and/or other calculi, objects, or other material from a body tract of a patient, such as biliary and pancreatic ducts, hepatic ducts, cystic duct, common bile duct, ureters, urinary bladder, urethra, and kidney.

Further, it is an object of the invention to provide a medical device capable of fragmenting a stone or other object in a body tract of a patient prior to removal. Finally, it is an object of the invention to provide a medical device capable of safe disengagement from the object being retrieved or fragmented and subsequent safe withdrawal of the device in case of failure of any of the components thereof during the procedure.

Accordingly, a medical device having a multi-wire retrieval basket which is releasable when an amount of force that is less than the amount of force required to cause failure of components of the retrieval device other than the tip joint is applied to the wires of the basket is disclosed herein.

In general, in one aspect, the invention features a medical device comprising a handle, a sheath, and a basket. The sheath, having a lumen formed therein, distally extends from the handle. In one embodiment of the invention, the basket consists of a plurality of wires having a proximal end and a distal end. The proximal ends of the basket wires are joined at a basket base and the distal ends of the basket wires are releasably joined by a tip joint. An elongate traction member may be axially disposed within the lumen of the sheath. In one embodiment, the traction member distally extends from the proximal end of the handle and is connected to the basket base. The traction member may comprise a cable, a coil, a shaft, a guidewire or a mandril wire. In one embodiment, the traction member and the basket wires may be formed from a single piece of material. In another embodiment, the proximal ends of the basket wires are joined at the basket base to the traction member by a proximal connector.

The tip joint is releasable from the distal end of the basket wires when the predetermined force, which is less than the force required to cause the traction member or at least one basket wire to fail, is applied to the tip joint.

Embodiments of this aspect of the invention include the following features. The tip joint may comprise an adhesive joint, a solder joint, a welded joint or an over-molding joint. In one embodiment, the tip joint comprises a tubular tip member. The lumen of the tubular tip member is adapted to receive the distal end of the basket therein. In a particular embodiment, the lumen of the tubular tip member is compressed around the basket wires thereby securing the distal end of the basket therein. At least one wire of the plurality of wires forming the basket is capable of sliding out of the tubular tip member when the predetermined force is applied to the tubular tip member so that the tubular tip member deforms. The predetermined force is less than the force required to cause the traction member or at least one wire of the plurality of wires forming the basket to fail. In one embodiment, the tubular tip member is made of, for example, sterling silver, silver, gold, platinum, stainless steel, or a nickel titanium alloy. In other embodiments, the tubular tip member is made of plastics.

In one embodiment of the invention, the basket is moveable between a withdrawn position in which the basket is collapsed within the lumen of the sheath, and an expanded position in which the basket extends from the distal end of the sheath and is disposed outside of the lumen for capturing the objects in the body. Movement of the basket between the expanded position and the withdrawn position causes the objects in the body captured in the basket to fragment.

In one embodiment of the invention, the handle includes at least one actuating mechanism. In a particular embodiment, the traction member is slideably moveable relative to the sheath when actuated by the actuating mechanism in the handle, which causes the traction member to shift the basket between the withdrawn position and the expanded position.

In another embodiment of the invention, the sheath is slideably moveable relative to the traction member. In this embodiment, the sheath is connected to the actuating mechanism at the handle, which causes the sheath to shift the basket between the withdrawn position and the expanded position.

The handle of the device according to the invention may be detachable. In one embodiment, the sheath is dimensioned to fit within a working channel of an endoscope. In one embodiment, the plurality of wires forming the basket is made of, for example, stainless steel or a nickel titanium alloy.

In general, in another aspect, the invention features a method for removing objects from a body tract, including the steps of providing a medical device as described above, introducing the medical device with the basket in the withdrawn position into the working channel of the endoscope; accessing the target body tract; shifting the basket into the expanded position; manipulating the basket to capture the objects therein; and withdrawing the medical device from the body tract. In a particular embodiment of this aspect of the invention, the method further includes the step of applying traction to the traction member in the proximal direction thereby generating tension within the basket and causing the captured objects to fragment. In another embodiment, the method further includes the step of applying traction to the sheath in the distal direction thereby generating tension within the basket and causing the captured objects to fragment. In some embodiments, the method also includes the step of injecting contrast material for fluoroscopic visualization.

BRIEF DESCRIPTION OF THE DRAWINGS

In the drawings like reference characters generally refer to the same parts throughout the different views. The drawings are not necessarily to scale, emphasis instead generally being placed upon illustrating the principles of the invention.

DESCRIPTION

All of the following disclosed embodiments of the medical retrieval device according to the invention generally have at least one thing in common, and that is that the tip of a multi-wire retrieval basket is releasable when an amount of tensile force that is less than the amount of force required to cause failure of components of the retrieval device other than the tip joint, for example, the traction member, is applied to the wires of the basket. Failure of one or more components of the retrieval device means that the component is no longer useful for its intended purpose, because of, for example, permanent deformation or breakage of the component. The retrieval basket of the invention is used to retrieve one or more stones and/or other calculi, objects, or other material from a body tract such as biliary and pancreatic ducts, hepatic ducts, cystic duct, common bile duct, ureters, urinary bladder, urethra, and kidney.

Figure 1A:
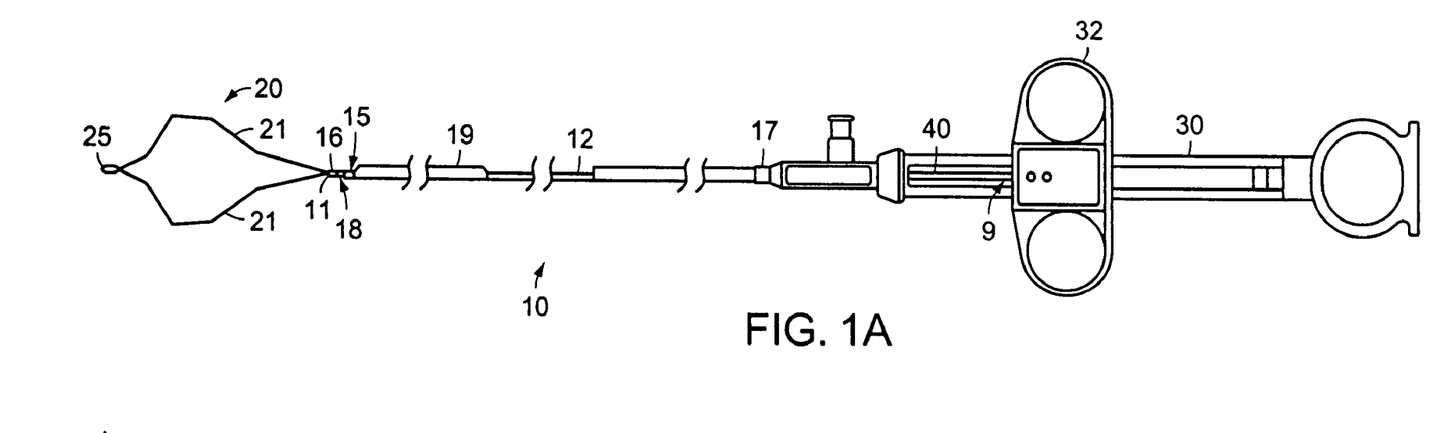
FIG. 1A illustrates an embodiment of a medical retrieval device according to the invention with the basket in the expanded position.
Figure 1B:
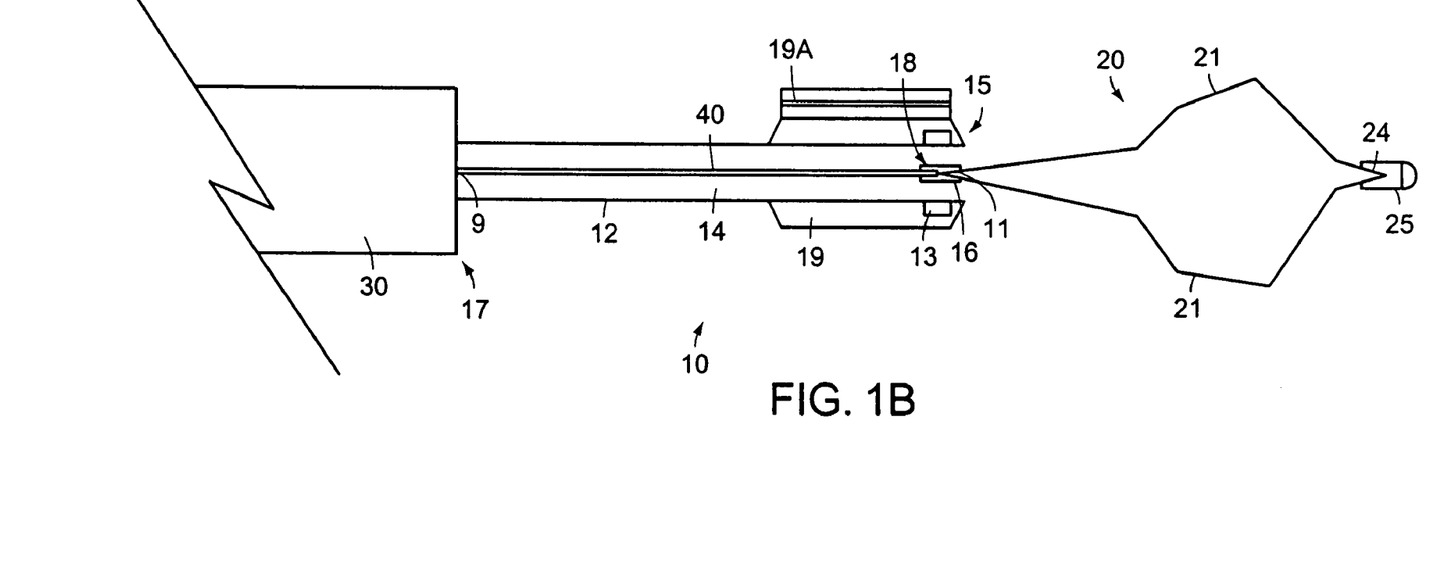
FIG. 1B illustrates an enlarged cross-sectional view of the basket and the sheath according to the embodiment of the invention illustrated in FIG. 1A with the basket in the expanded position.
Figure 1C:
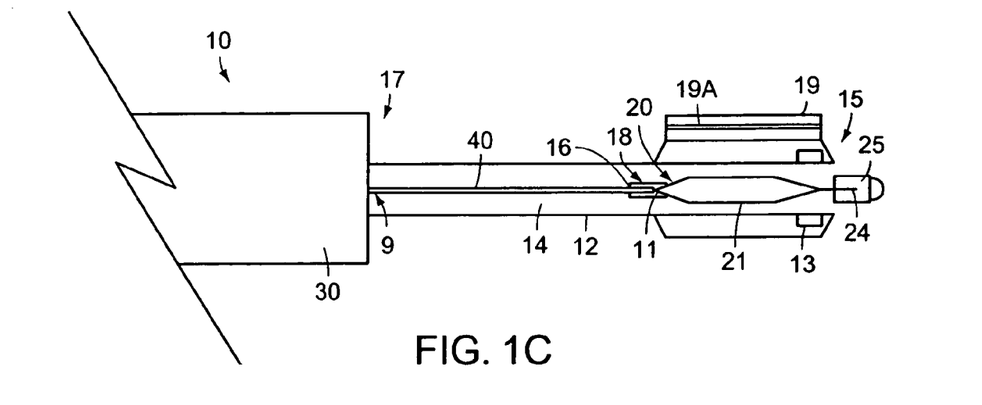
FIG. 1C illustrates an enlarged cross-sectional view of the basket and the sheath according to the embodiment of the invention illustrated in FIG. 1A with the basket in the withdrawn position.

Referring to FIGS. 1A-1C, the medical device 10, according to the invention, includes a handle 30, a catheter, such as a sheath 12, and a retrieval basket 20 slideably moveable in the sheath 12. Alternatively, the retrieval basket 20 can be fixed in a stationary position with the sheath 12 configured to be slideably moveable to expose (FIGS. 1A-1B) and cover/collapse (FIG. 1C) the basket 20. The retrieval basket 20 is flexibly connected to one or more elongated traction members 40 by a proximal connector 16. Alternatively, the retrieval basket 20 and one or more traction members 40 can be made from a single piece of material. The retrieval basket 20 is of a type that can be collapsed within a sheath 12 for entry into the body. In general, the handle 30, sheath 12, and retrieval basket 20 illustrated in FIGS. 1A-1C are not necessarily shown in their correct size or proportion to each other. In one embodiment, the handle 30 is detachable from the rest of device 10 without disassembly of the entire device 10, and a new handle 30 may be attached. In one embodiment, the handle and catheter assembly must be compatible with and attachable to a handle system, such as Alliance II™ Inflation System, manufactured by Boston Scientific Corporation of Natick, Mass., without disassembly. In another embodiment, the basket and the traction member must be compatible with and attachable to a mechanical lithotripsy system by removing the handle 30 and the sheath 12, and attaching the traction member 40 to the handle of the lithotripsy system.

The size of the entire sheath 12 is dimensioned to fit the requirements of the application of the sheath 12 in the body. For example, for most biliary type applications, the working length of the device 10 from the distal end 15 of the sheath 12 to the distal end 17 of the handle 30 ranges from about 60 inches (150 cm) to about 120 inches (300 cm), preferably about 70.9 inches (180+/−0.5 cm). In one embodiment, the size of the basket 20 and sheath 12 is dimensioned to fit in a 3.2 mm diameter or larger working channel of an endoscope, such as duodenoscope.

Referring to FIGS. 1B-1C, the sheath 12 has at least one lumen 14 therein that extends from the handle 30 to the distal end of the sheath 15. In one embodiment of the invention, the sheath 12 includes a wire coil reinforced tube terminated distally by a reinforcement ring, such as a stainless steel reinforcement ring 13 illustrated in FIGS. 1B and 1C. In a particular embodiment of the invention, the reinforcement ring is made of 303 stainless steel. The wire coil is made of stainless steel, for example, 304 stainless steel, and is coated with polytetrafluoroethylene (PTFE) to provide a low friction surface. As one of ordinary skill would appreciate, the 300 series stainless steels are nickel-chromium austenitic steels with low carbon content. Particularly, 303 stainless steel typically contains 17-19% chromium, 8-10% nickel, 0.15-0.45% sulfur, no more than 0.15% carbon, no more than 2% manganese, no more than 0.02% phosphorus, no more than 0.6% molybdenum, and no more than 1% silicone with balance iron. Further, 304 stainless steel typically contains 18-20% chromium, 8-10.5% nickel, no more than 0.03% sulfur, no more than 0.08% carbon, no more than 2% manganese, no more than 0.45% phosphorus, and no more than 1% silicone with balance iron.

The device 10 can be used in conjunction with a guidewire, such as, for example, a 0.035 Jagwire™ guidewire available from Boston Scientific Corporation of Natick, Mass. In such embodiment, the sheath 12 also includes a sidecar 19 located at the distal end 15 of the sheath 12 extending proximally therefrom. The sidecar 19 has a lumen 19a therein adapted to receive a guidewire. The lumen 19a may be lined with polytetrafluoroethylene (PTFE), perfluroethylenepropylene (FEP), or similar coating. The ends of the sidecar 19 are tapered to promote cannulation and withdrawal and to avoid inflicting trauma to surrounding tissues. In a particular embodiment of the invention, the diameter of the lumen 19a of the sidecar 19 is in the range of about 0.035 inches to 0.040 inches, preferably 0.038 inches; and the length of the sidecar is in the range of about 7 inches to about 10 inches, preferably 8.25 inches.

An elongated traction member 40 can be a cable, coil, shaft, guidewire or mandril wire 40 and extends within the lumen 14 of the sheath 12 from the handle 30. In a particular embodiment, the traction member 40 is a 304 stainless steel wire. In one embodiment, the traction member 40 is joined at its proximal end 9 to at least one actuating mechanism 32 at the device handle 30. In another embodiment, the traction member 40 can be joined at its distal end 18 to the base 11 of the retrieval basket by a proximal connector 16. In yet another embodiment, the traction member 40 and the basket wires 21 are formed from a single piece of material.

Referring now to FIGS. 1A, 1B and 1C, operation of one or more actuating mechanisms 32 on the handle 30 by an operator causes the traction member 40 to slideably move in the sheath 12 causing the retrieval basket 20 to move in and out of the sheath 12. Alternatively, the mechanism 32 can cause movement of the sheath 12 to advance the sheath 12 over the stationary retrieval basket 20 and traction member 40 combination to thereby collapse the retrieval basket 20 within the sheath 12, and the mechanism 32 can slide the moveable sheath 12 back to expose the stationary retrieval basket 20 and allow it to open/expand. In general, both types of retrieval basket/sheath movement configurations and related handle mechanisms are known, and can be seen in existing product designs available from, for example, Boston Scientific Corporation of Natick, Mass.

Figure 2:
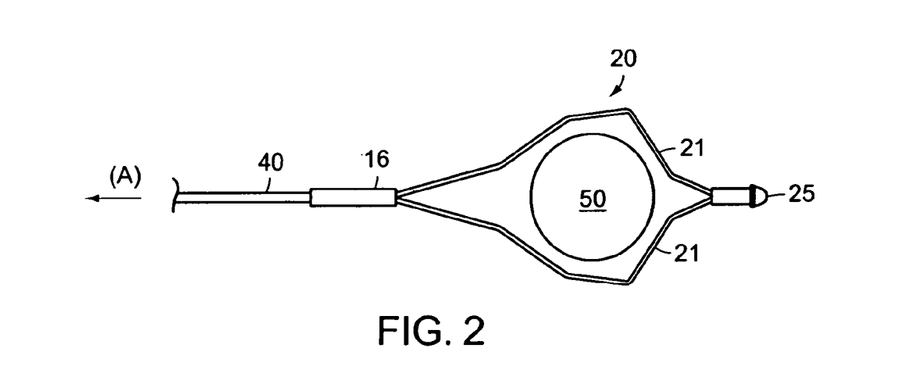
FIG. 2 illustrates a basket with a captured stone, the basket extended from the sheath.

With the retrieval basket 20 collapsed within the sheath 12 as shown in FIG. 1C, the sheath 12 can be inserted into the body by an operator to a site in the body where the stone or stones to be retrieved are located (e.g., a stone in the common bile duct). By placing the retrieval basket 20 into its expanded position, as illustrated in FIGS. 1A, 1B, and 2, the retrieval basket 20 can be manipulated by the operator to entrap or capture a stone within the retrieval basket 20. In some clinical situations it is desirable to fragment the captured stone(s). For example, when the combination of the stone and basket 20 is too large to be withdrawn atraumatically from the body tract, the stone may be fragmented by, for example, mechanical lithotripsy.

Figure 3:
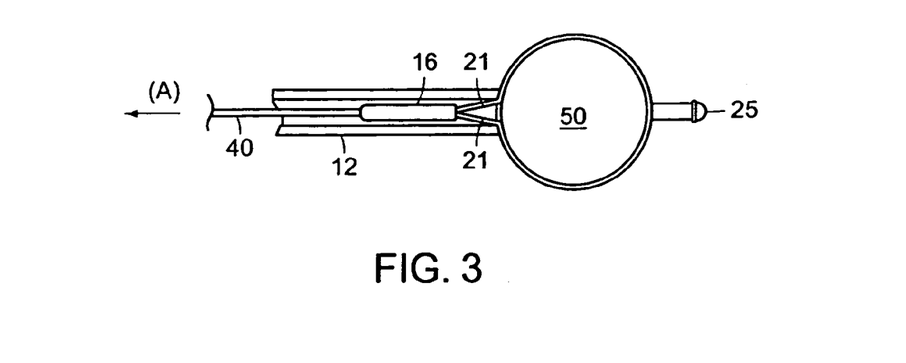
FIG. 3 illustrates a basket with a captured stone, the basket partially withdrawn into the distal end of the sheath.

Referring now to FIGS. 2 and 3, according to the invention, the stone 50 is fragmented by applying traction on the traction member 40 in a proximal direction indicated by arrow a in FIG. 2. Referring to FIG. 3, as traction is applied to traction member 40, the basket wires 21 tend to collapse around the stone 50 as the retrieval basket 20 enters the sheath 12. As an increasing amount of traction is applied to the traction member 40, the basket wires 21 tighten around the stone 50 until the tension generated in the wires 21 is sufficient to crush or fragment the stone 50.

Figure 4:
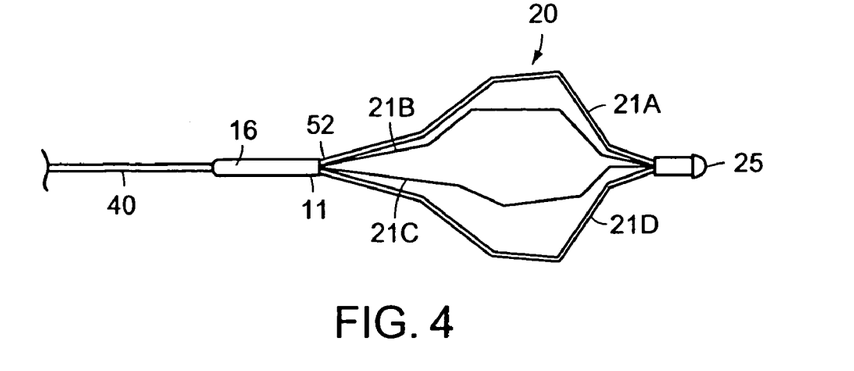
FIG. 4 illustrates an embodiment of a retrieval basket according to the invention.

Referring to FIG. 4, in one embodiment, the retrieval basket 20 is composed of a plurality of wires 21, such as four wires 21a, 21b, 21c, 21d spaced at 90 degree angle apart from each other that are bent or formed to provide the desired basket shape. The basket wires 21 in one embodiment are round, or alternatively, rectangular in cross section. Other cross-sectional wire shapes are also contemplated by the invention, such as D-shaped or V-shaped. In one embodiment, each of wires 21 is formed with four bends so that the width of the basket 20 in its expanded position is greater at the distal end 24 of the wires 21 than at the proximal end 11 of the retrieval basket 20 to ease effective capture of stones 50. The basket wires 21 may be manufactured from stainless steel, nickel titanium, other metal alloys, or other materials or combinations of materials known in the art suitable for basket wires. In a particular embodiment of the invention, the basket wires are manufactured from a nickel-titanium alloy containing between 54% and 57.5% nickel with balance titanium. In one embodiment of the invention, the radial stiffness of the basket wires 21 is greater than 0.7 g/mm. In another embodiment of the invention the radial stiffness of the basket wires 21 is greater than 1.0 g/mm.

Other numbers of basket wires and other wire shapes are also contemplated by the invention other than the four bent wires illustrated in FIG. 4. The typical dimensions for a retrieval basket 20 for biliary applications, according to the invention, range from about 0.6 inches (1.5 cm) in diameter by about 1.8 inches (3 cm) in length to about 1.8 inches (3 cm) in diameter by about 2.36 inches (6.0 cm) in length. Preferably, the basket dimensions in one embodiment are about 0.6 inches (1.5 cm) in diameter by about 1.18 inches (3.0 cm) in length, in another embodiment, about 0.79 inches (2.0 cm) in diameter by about 1.58 inches (4.0 cm) in length, in another embodiment, about 1.0 inch (2.5 cm) in diameter by about 1.97 inches (5.0 cm) in length, and in yet another embodiment, 1.18 inches (3.0 cm) in diameter by about 2.36 inches (6.0 cm) in length. The dimensions of the retrieval basket 20 may be smaller or larger depending on the application of the retrieval basket 20 in the body. For example, the dimensions of the retrieval basket 20 used for typical urinary tract applications may be smaller than the basket used for biliary applications.

Figure 5A:
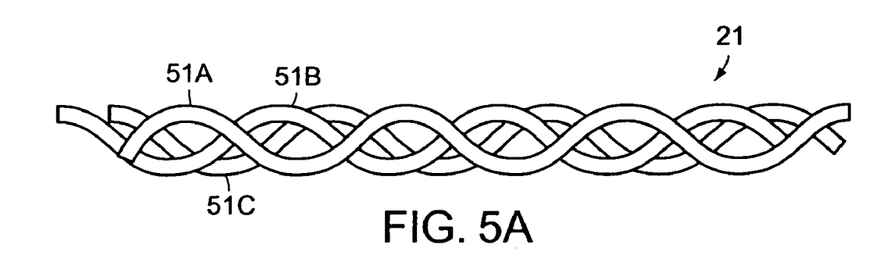
FIG. 5A illustrates an enlarged view of the structure of the basket wire according to one embodiment of the invention.
Figure 5B:
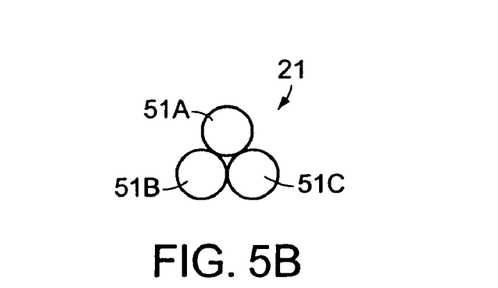
FIG. 5B illustrates a sectional view of the basket wire according to the embodiment the invention shown in FIG. 5A.

In one embodiment, illustrated in FIGS. 5A and 5B, for example, each of the basket wires 21 are manufactured from three filaments 51a, 51b, and 51c of 0.0085 inch PRECURSOR nickel titanium alloy twisted together into a single stranded cable 21.

The stones 50 that may be fragmented by the retrieval basket 20 according to the invention may vary in size from about 0.2 inches (0.5 cm) in diameter up to about 1.18 inches (3.0 cm) in diameter and vary in physical characteristics as soft, such as cholesterol stones 50, to hard, such as bilirubin stones 50. In one embodiment of the invention, the retrieval basket 20 is a four-wire basket capable of capturing up to five separate stones 50 for simple extraction without fragmenting the stones 50. In one embodiment, the retrieval basket 20 is capable of capturing up to five separate stones 50 for simple extraction without fragmenting the stones 50 where the force applied to the retrieval basket 20 does not exceed 20 pounds. In another embodiment, the retrieval basket 20 is capable of capturing up to five separate stones 50 for simple extraction without fragmenting the stones 50 where the force applied to the handle during each stone capture is a minimum of 15 pounds.

In one embodiment, the retrieval basket 20 is capable of fragmenting at least two separate stones 50 where the force applied to the handle during each capture does not exceed the range of 25-50 pounds. In a particular embodiment, the retrieval basket 20 is capable of fragmenting at least two stones at a force that does not exceed 35 pounds for either stone. In another embodiment, the retrieval basket 20 is capable of fragmenting at least two separate stones 50 where the force applied to the handle during fragmenting of a first stone is at least 36 pounds, and the force applied to the handle during fragmenting of a second stone is at least 25 pounds. Following fragmentation of one or more stones 50, the retrieval basket 20 is fully capable of being fully collapsed in the lumen 14 of the sheath 12.

Referring again to FIG. 4, in one embodiment of the invention, the basket wires 21a, 21b, 21c, 21d of the retrieval basket 20 are joined at their proximal ends at the base 11 of the retrieval basket 20 by, for example, a proximal connector 16.

In one embodiment, the proximal connector 16 comprises a tube having a lumen extending longitudinally therethrough. The proximal connector 16 is swaged to hold the wires 21a, 21b, 21c, 21d together tightly. Other methods of joining the wires 21a, 21b, 21c, 21d known in the art such as adhesives, solder, welding, binding, or overmolding, or by any of their combination with or without proximal connector 16 may be used to join or gather together the proximal ends 52 of basket wires 21 at the basket base 11. In one embodiment of the invention, the proximal connector 16 is made of 303 stainless steel and is joined to a 304 stainless steel traction member 40.

Figure 6A:
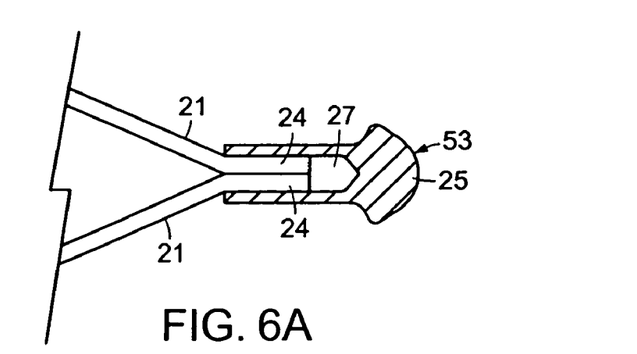
FIG. 6A illustrates an embodiment of the tip joint of the retrieval basket according to the invention.
Figure 6B:
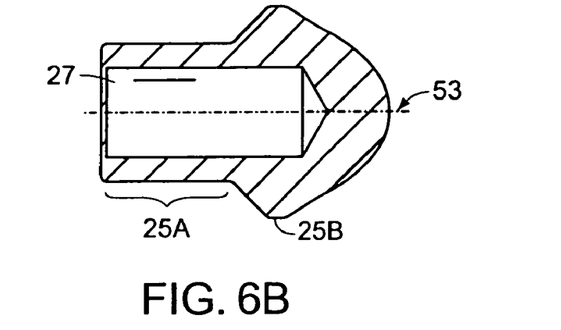
FIG. 6B illustrates an enlarged cross-sectional view of the tip joint of the retrieval basket according to the embodiment of the invention shown in FIG. 6A

Referring now to FIG. 6A, according to the invention, the distal ends 24 of the basket wires 21 are gathered together and held in place by a tip joint 25. In one embodiment of the invention, tip joint 25 is a tubular tip member, for example, as illustrated in FIGS. 6A and 6B. The tubular tip member 25 comprises a tube having a lumen 27 extending longitudinally through the tube. The tubular tip member 25 may be manufactured from materials such as sterling silver, coin silver or other silver-based alloys, pure silver, gold, platinum, stainless steel, nickel titanium, other metal alloys, or plastics. The material for the tubular tip member is chosen to fit the requirements of the application of the retrieval basket in the body. For example, if the tubular tip member 25 is manufactured from a silver-based alloy, for example silver/copper alloy, a higher percentage of silver would result in a softer alloy. As a result, the tubular tip member 25 will release from the basket wires 21 at a release force that is lower than that of the tubular tip member of identical dimensions made from an alloy with a lower percentage of silver. In one embodiment, the tubular tip member 25 is sealed at its distal end 53.

In a particular embodiment of a biliary-type retrieval basket 20 illustrated in FIG. 1A, the tubular tip member 25 is releasable at a predetermined force from the distal ends 24 of the basket wires 21. Referring to FIG. 6B, the tubular tip member 25 may be manufactured from sterling silver. The overall length of the tubular tip member 25 is 0.123 inches and the diameter at the narrowest region 25a is 0.0510 to 0.0520 inches. The inside diameter of the lumen 27 is 0.0352 to 0.0358 inches. The length of the lumen 27 is about 0.086 inches. The distal ends 24 of the basket wires 21 are inserted 0.0545 to 0.688 inches into the lumen 27 of the tubular tip member 25. The diameter of the tubular tip member at the widest region 25b is 0.085 inches. The distal end 53 of the tubular tip member 25 has a spherico-conical shape to ease cannulation and reduce the risk of trauma to surrounding tissue. The radius of the distal end 53 of the tubular tip member 25 is 0.030 inches.

Referring again to FIG. 6A, in one embodiment of the tip joint 25 of the invention, the distal ends 24 of the basket wires 21 are gripped by the tubular member 25 because the tip member 25 is reduced in diameter, i.e. swaged, to cause the wire ends 24 to be compressed together. In other embodiments of the invention, the distal ends 24 of the wires 21 may be joined by adhesives, solder, welding, over-molding, or other means of binding, or by any combination of joining methods, with or without a tubular tip member 25. All of the embodiments of the distal ends 24 of the wires 21 have in common the feature that the distal ends 24 are releasable when a predetermined force is applied to the tip joint 25 causing the tip joint 25 to become disengaged from the wires 21.

Figure 7A:
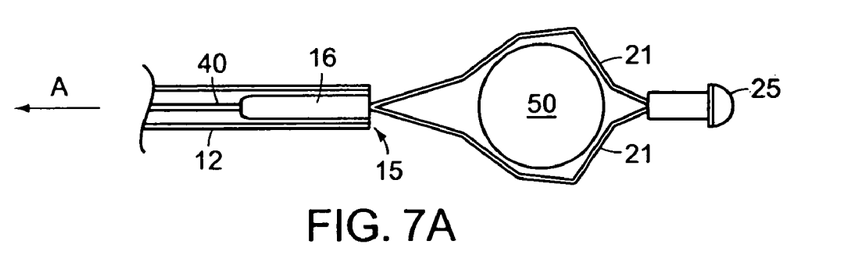
FIG. 7A illustrates a step in releasing a captured stone from the retrieval device according to the invention.
Figure 7B:
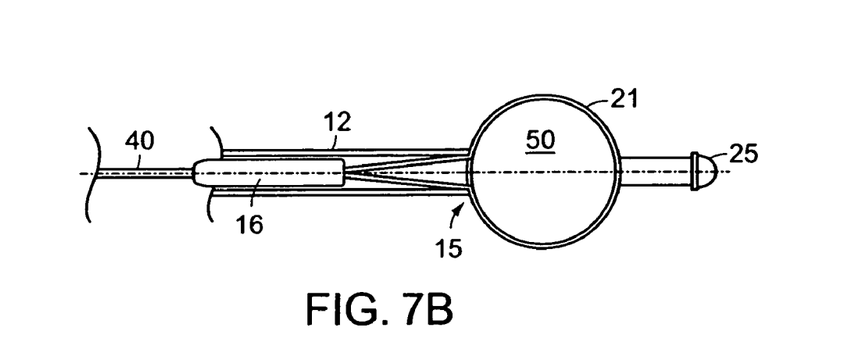
FIG. 7B illustrates another step in releasing a captured stone from the retrieval device according to the invention.
Figure 7C:
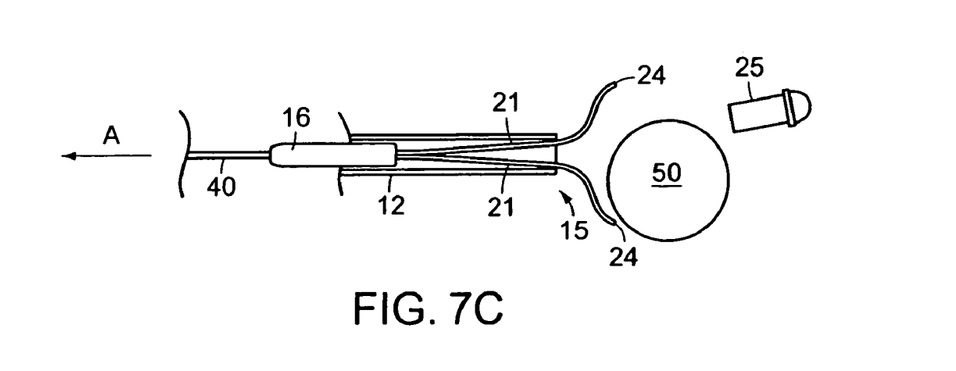
FIG. 7C illustrates another step in releasing a captured stone from the retrieval device according to the invention.

Referring to FIGS. 7A, 7B, 7C, and 7D, in order to overcome the problems caused when a component of a medical retrieval device 10 breaks during retrieval of the stone 50 from a body tract, the tip joint 25, according to the invention has an interface which is releasable. By releasing the tip joint 25, the distal ends 24 of the basket wires 21 are freed, i.e. no longer joined together. With the distal ends 24 of the basket wires 21 free, the distal end of the retrieval basket 20 is open, as shown in FIG. 7C. To illustrate this point more clearly, referring to FIG. 7A, the retrieval basket 20 with captured stone 50 is shown extended beyond the distal end 15 of the sheath 12 in its expanded configuration. The retrieval basket 20 has a releasable tubular member 25 according to the invention.

Referring now to FIG. 7B, as traction is applied to traction member 40, the basket wires 21 tend to collapse around the stone 50 as the retrieval basket 20 enters the sheath 12. As an increasing amount of traction is applied to the traction member 40, the basket wires 21 tighten around the stone 50.

Referring to FIG. 7C, to release the stone 50, an operator applies tension to traction member 40 by pulling on traction member 40 in the proximal direction indicated by the arrow a. As basket wires 21 enter the distal end 15 of the sheath 12, a load generated at the tip joint 25 of the retrieval basket 20 that is less than the load that would cause one or more basket wires 21 to fail or break, but sufficient to cause deformation of the tubular tip member 25. When the tubular tip member 25 deforms, it loosens the grip of the basket wires 21 thereby allowing the distal ends 24 of the basket wires 21 to slide out of the tubular member 25. In one embodiment, the load required to cause the retrieval basket 20 to fail at the tip joint 25 is in the range of about 20 to 50 pounds at the basket tip. In a particular embodiment, the load required to cause the retrieval basket 20 to fail at the tip joint 25 is about 42 pounds.

Figure 7D:
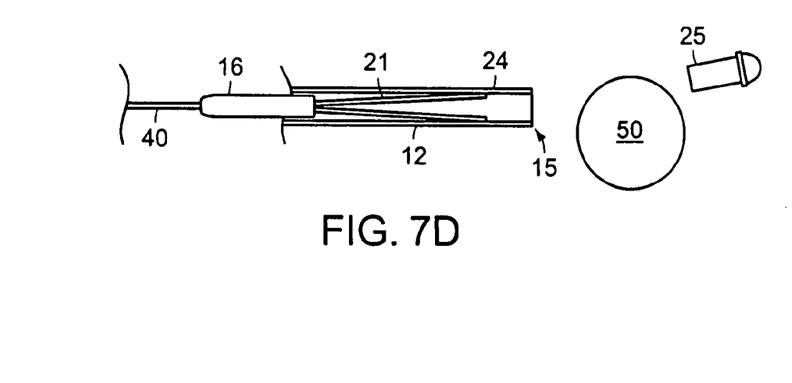
FIG. 7D illustrates another step in releasing a captured stone from the retrieval device according to the invention.

Thus, as illustrated in FIG. 7C, the distal ends 24 of the basket wires 21, slide out of tubular member 25 as the retrieval basket 20 is withdrawn further into the sheath 12. The stone 50, illustrated in FIG. 7C, is released from the retrieval basket 20 through the basket distal end. Referring to FIG. 7D, the retrieval basket 20 is withdrawn further into sheath 12 until the distal ends 24 of the basket wires 21 are retained within the sheath 12. With the basket wires 21 retained by sheath 12, the medical retrieval device 10 can be safely withdrawn from the body tract.

To ensure safe release of the stone 50 in overload conditions during stone retrieval, the retrieval basket distal tip joint 25 fails at a load that is less than the load which would cause any other component in the device 10, such as the traction member 40, to fail. The tip joint 25 is strong enough to perform the task for which the device 10 is intended, i.e., stone retrieval or reducing the size of the stone. The design of the device 10 must take the variation in strength of each component and joint of the retrieval device 10 into consideration to ensure that the that the tip joint 25 will fail at a lower load than will any other component or joint of the device 10.

Figure 8:
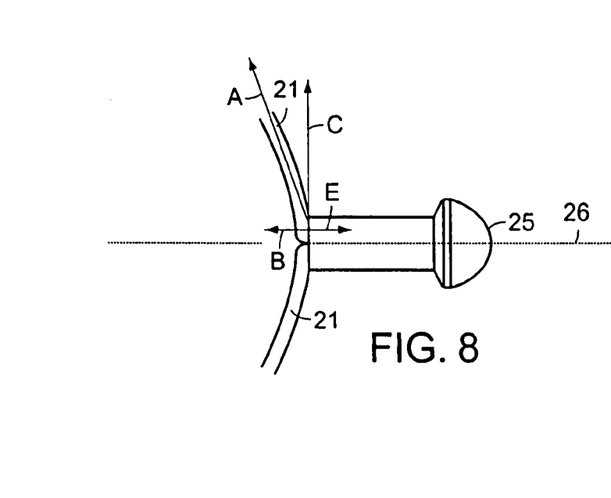
FIG. 8 illustrates the forces acting on the tip joint of the retrieval basket according to the invention.

FIG. 8 illustrates distribution of forces acting on the distal end 24 of the basket wires 21 restrained by a tip joint such as the tubular tip member 25. Tension, indicated by arrow a, on basket wires 21 is resolved into a force component B, indicated by arrow b that is aligned with the long axis 26 of the tubular tip member 25 and a force component C indicated by arrow c that is at an angle nearly perpendicular to the long axis 26 of the tubular tip member 25. The force component indicated by arrow b that is aligned with the long axis 26 of tip member 25 is resisted by the retention force E indicated by arrow e generated by the tubular tip member 25 on the basket wires 21. If the force component B aligned with the long axis 26 of the tubular tip member 25 exceeds the available retention force E, the basket wires 21 will slide out of the tubular tip member 25 and release the stone 50.

Retention force E, indicated by arrow e in FIG. 8, is a result of friction between the basket wires 21 and the tubular tip member 25. The friction between the basket wires 21 and the tubular tip member 25 is influenced by the pressure exerted on the distal ends 24 of the wires 21 by the tubular tip member 25, the surface form of the interior of the tubular tip member 25, the exterior of the basket wires 21, the physical dimensions of the tubular tip member 25, and the distance the distal ends 24 of the basket wires 21 are inserted within the tubular tip member 25. The force component C indicated by arrow c that is at an angle nearly perpendicular to the long axis 26 of the tubular tip member 25, acts upon the tubular tip member 25 to reduce the pressure exerted upon the basket wires 21, which reduces the friction and resulting retention force E indicated by arrow e in FIG. 8. As the tension A increases, the tubular tip member 25 begins to deform and, as a result, retention force E reduces. If the combined components of the basket wire tension cause the retention force E to be exceeded by the aligned force B, and the total tensile load on the basket wires 21 is less than their failure load, the basket wires 21 will be released from the tip joint 25.

The amount of force required to cause tubular tip member 25 to release may also be changed, for example, by varying the crimp length of the tip, varying the thickness of the wall of the tubular region of the tip comprising the crimp, or by scoring the distal ends 24 of the basket wires 21.

Although the description above describes the action of basket wire tension upon a tubular tip member 25, a similar effect can be produced with other methods of joining the basket wires 21 where the forces acting upon the tip joint 25 exceed the strength of the tip joint 25 without exceeding the strength of the basket wires 21. For example, if the basket wires 21 are joined by welding, the weld joint 25 can be designed to fail at a load that is less than the load required to cause the basket wires 21 to fail. Because welding typically causes a localized reduction in the strength of the welded material, such a tip joint 25 can be readily produced. Alternatively, the basket wires 21 may be joined by an adhesive or solder where the mechanical properties of the adhesive or solder material will allow failure of the tip joint 25 at a load that is lower than the failure load of basket wire 21. Alternatively yet, the basket wires 21 may be joined by forming a tip joint 25 around the distal ends 24 of the wires by molding or casting a meltable material such as metal or thermoplastic, or by molding a curable liquid, such as a thermosetting polymer or epoxy around the distal ends 24 of the basket wires 21. The joining method and materials used are dictated largely by the loading requirements of the medical device 10. For example, with respect to medical devices intended for simple stone retrieval without lithotripsy, the sheath 12 and retrieval basket 20 are constructed of lighter and more flexible materials to allow easier capture of the stone 50. Because the strength of components comprising such a device is low as compared to devices intended for lithotripsy, the basket wire 21 could be joined at the distal tip joint 25 by adhesive, which would allow release of the stone 50 at a more modest load.

Figure 9:
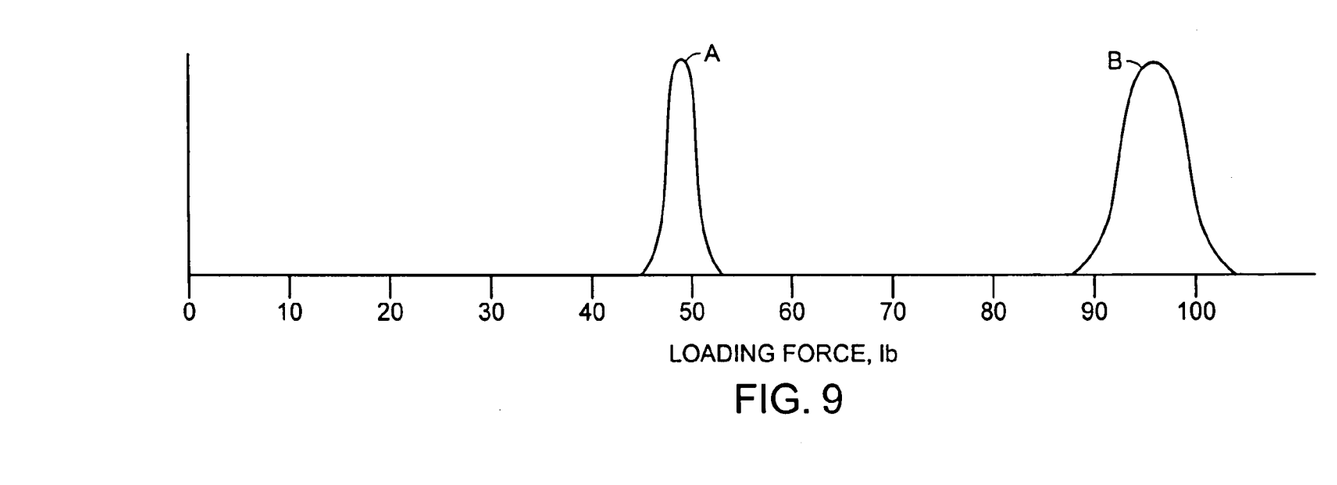
FIG. 9 graphically illustrates failure load for the tip joint compared to failure load for all other components of the retrieval device according to the invention.

FIG. 9 illustrates the design rationale of the medical retrieval device according to the invention including a retrieval basket 20 with a releasable tip joint 25. Curve A illustrates the distribution of basket tip joint 25 failure forces and curve B illustrates the distribution of the failure forces of all other components of the medical retrieval device 10. The distribution of failure forces for basket tip joint 25 is sufficiently lower than the distribution of failure forces for all other components of device 10. Thus, the probability that the basket tip joint 25 strength exceeds the strength of any other component of the device 10 is exceedingly small.

In another aspect of the invention, the medical device 10, including the retrieval basket 20 according to the invention, is used in a method for removing stones 50 from a body tract.

The body tract may be any cavity in the body including but not limited to pancreatic ducts, biliary ducts including the hepatic ducts, cystic duct, and common bile duct, ureter, urethra, urinary bladder and kidney.

Referring again to FIGS. 1A-1C and 7A-7D, in this aspect of the invention, in general, an operator inserts the medical device 10 according to the invention including retrieval basket 20 into the working channel of an endoscope with the retrieval basket 20 in the closed position within sheath 12 as illustrated in FIG. 1A. The medical device 10 alternatively may be passed over a 0.035 inch guidewire, such as a Jagwire™ guidewire, manufactured by Boston Scientific Corporation of Natick, Mass., using a sidecar 19, through the working channel of the endoscope. Once the device has accessed the body tract of interest, typically an injection of contrast material is made for fluoroscopic visualization. When the retrieval basket 20 approaches the stone or stones 50 to be captured and fragmented, the traction member 40 is advanced distally (in the direction away from the operator) advancing retrieval basket 20 into its expanded configuration where the retrieval basket 20 is no longer restrained by sheath 12. The retrieval basket 20 assumes its expanded configuration outside the distal end 15 of the sheath 12. Then, the operator maneuvers the expanded retrieval basket 20 around stone 50 until stone 50 passes between the basket wires 21 into the retrieval basket 20. Generally, after a stone 50 is captured in the retrieval basket 20, the medical retrieval device 10 including the retrieval basket 20 and captured stone 50 is withdrawn through the body tract. If the combination of the stone 50 and retrieval basket 20 is too large to be withdrawn from the body tract, the stone 50 must be reduced in size or released from the basket 20. To reduce the size of the stone 50 according to the invention, the stone 50 is fragmented by applying traction in the proximal direction to traction member 40 by actuating mechanism 32 forcing basket wires 21 to tighten around stone 50. The degree of force applied to traction member 40 is increased to generate sufficient tension within basket wires 21 to cause the stone 50 to fragment. If additional tension is required to facilitate lithotripsy, the handle 30 may be attached to an Alliance II™ Inflation System, manufactured by Boston Scientific Corporation of Natick, Mass., or to a mechanical lithotripsy system by removing the handle 30 and the sheath 12, and attaching the traction member 40 to the handle of the lithotripsy system. Additional tension may be required when the actuating mechanism 32 in the handle 30 is unable to generate sufficient tension in the basket wires 21, where, for example, the retrieval basket 20 is in almost collapsed position when the stone 50 is captured because of the small size of the stone 50.

According to the invention, when the tension needed to fragment the stone 50 approaches the force that would cause any component of the device 10 to fail, the tip joint 25 fails first. In some cases, however, the traction member 40 may fail at the distal end 17 of the handle 30, where, for example, a particular path of the catheter in the patient's body tract results in an increased friction at the proximal end 9 of the traction member 40. If the traction member 40 so fails, a mechanical lithotripsy system can be attached to the traction member 40 by removing the handle 30 and the sheath 12, and attaching the traction member 40 to the handle of the lithotripsy system to provide tension to the basket wires 21 to fragment the stone 50 or achieve the release of the tip joint 25 when the tension needed to fragment the stone 50 approaches the force that would cause any component of the medical device 10 to fail.

According to one embodiment of the invention, the tip joint 25 fails when the distal ends 24 of basket wires 21 are freed by releasing tubular tip member 25 as illustrated in FIGS. 7C-7D. As the operator applies traction in the proximal direction on the traction member 40, the tubular tip member 25 is released from the distal ends 24 of the basket wires 21 when the force applied to the basket wires 21 through the traction member 40 is less than the force required to cause the basket wires 21 to break, but great enough to cause tubular tip member 25 to deform thereby allowing basket wires 21 to slide out of tubular tip member 25. In one embodiment of the invention, the force required to cause tip member 25 to be released from the distal ends 24 of the basket wires 21 is in the range of about 20 to 50 pounds at the basket tip.

It will be apparent to those skilled in the art of medical stone retrieval that various modifications and variations can be made to the above-described structure and methodology without departing from the scope or spirit of the invention.

The invention claimed is:

1. A medical device, comprising:
   a sheath comprising a proximal end and a distal end;
   a handle at the proximal end of the sheath; and
   a basket having a collapsed position when the basket is within the sheath and collapsed and an expanded position when the basket is positioned beyond the distal end of the sheath and expanded, the basket comprising a plurality of wires, a proximal end, and a distal end where the distal ends of the plurality of wires are joined at a joint configured to fail when a first predetermined force is applied to the joint, the distal ends of the plurality of wires releasing from each other when the joint fails, the first predetermined force being less than both a force required to cause one of the plurality of wires to fail and a force required to cause the proximal end of the basket to fail;
   wherein the basket distal end comprises a tip member, and the tip member releases from the plurality of wires when the joint fails.

2. The device of claim 1, wherein a cross-section of at least one of the plurality of wires is D-shaped.

3. The device of claim 1, wherein a cross-section of at least one of the plurality of wires is V-shaped.

4. The device of claim 1, each of the plurality of wires comprises a proximal end and a distal end, the distal end of at least one wire is scored.

5. The device of claim 1, wherein each of the plurality of wires comprises four bends.

6. The device of claim 1, wherein the basket in the expanded position is wider at the distal end than at the proximal end.

7. The device of claim 1, wherein the radial stiffness of at least one wire is greater than 0.7 g/mm.

8. The device of claim 1, wherein the basket distal end comprises at least one of a weld joint, an over-molding joint, an adhesive joint, or a solder joint.

9. The device of claim 1, wherein the handle is detachable.

10. The medical device of claim 1, wherein:
    the joint applies a retention force on the plurality of wires;
    the plurality of wires applies a tension force on the joint when force is applied to the basket; and
    the tension force exceeds the retention force when the force applied to the basket exceeds the first predetermined force.

11. A medical device, comprising:
    a sheath comprising a proximal end and a distal end;
    a handle at the proximal end of the sheath; and
    a basket having a collapsed position when the basket is within the sheath and collapsed and an expanded position when the basket is positioned beyond the distal end of the sheath and expanded, the basket comprising a plurality of wires, a proximal end, and a distal end where the distal ends of the plurality of wires are joined at a joint configured to fail when a first predetermined force is applied to the joint, the distal ends of the plurality of wires releasing from each other when the joint fails, the first predetermined force being less than both a force required to cause one of the plurality of wires to fail and a force required to cause the proximal end of the basket to fail;

wherein the basket distal end comprises a tip member; and wherein the tip member is tubular and comprises a proximal end, a distal end, and a lumen extending at least partially therethrough, the lumen of the tubular tip member is adapted to receive an end of the basket wires therein.

12. The device of claim 11, wherein the tip member is sealed at the distal end.

13. The device of claim 11, wherein the distal end of the tip member has a spherico-conical shape.

14. A medical device, comprising:
a sheath comprising a proximal end and a distal end;
a handle at the proximal end of the sheath; and
a basket having a collapsed position when the basket is positioned within the sheath and an expanded position when the basket is positioned beyond the distal end of the sheath, the basket comprising a plurality of wires having respective proximal ends joined at a proximal joint and respective distal ends joined at a distal joint, wherein the distal joint is configured to fail when a first predetermined force is applied to the basket, the proximal end is configured to fail when a second predetermined force is applied to the basket, and at least one of the plurality of wires is configured to fail at a third predetermined force, the first predetermined force being less than the second and third predetermined forces;
wherein the basket distal end comprises a tip member, and the tip member releases from the plurality of wires when the distal joint fails.

15. The medical device of claim 14, wherein:
the distal joint applies a retention force on the plurality of wires;
the plurality of wires applies a tension force on the distal joint when force is applied to the basket; and
the tension force exceeds the retention force when the force applied to the basket exceeds the first predetermined force.

16. The medical device of claim 14, wherein the distal joint is at least one of a weld joint, an over-molding joint, an adhesive joint, or a solder joint.

17. A medical device, comprising:
a sheath comprising a proximal end and a distal end;
a handle at the proximal end of the sheath; and
a basket having a collapsed position when the basket is positioned within the sheath and an expanded position when the basket is positioned beyond the distal end of the sheath, the basket comprising a plurality of wires having respective proximal ends joined at a proximal joint and respective distal ends joined at a distal joint, wherein the distal joint is configured to fail when a first predetermined force is applied to the basket, the proximal end is configured to fail when a second predetermined force is applied to the basket, and at least one of the plurality of wires is configured to fail at a third predetermined force, the first predetermined force being less than the second and third predetermined forces, wherein:

the distal joint includes a tubular tip member having a lumen extending at least partially therethrough;
the respective distal ends of the plurality of wires are disposed within the lumen; and
the tip member exerts a pressure on the respective distal ends of the plurality of wires disposed within the lumen.

18. The medical device of claim 17, wherein:
the distal joint applies a retention force on the plurality of wires as a function of the exerted pressure;
the plurality of wires applies a tension force on the distal joint when force is applied to the basket; and
the tension force exceeds the retention force when the force applied to the basket exceeds the first predetermined force.

19. A medical device, comprising:
a sheath comprising a proximal end and a distal end;
a handle at the proximal end of the sheath;
a basket having a collapsed position when the basket is positioned within the sheath and an expanded position when the basket is positioned beyond the distal end of the sheath, the basket having respective proximal and distal ends comprising a plurality of wires having respective proximal and distal ends, the wires configured to fail when a first predetermined force is applied to the basket; and
a tubular tip member having a lumen at least partially extending therethrough and surrounding at least a portion of each distal end of each of the plurality of wires, the tip member configured to exert a pressure on the plurality of wires to retain the wires within the lumen;
wherein the tip member is configured to fail when a second predetermined force is applied to the basket, the second predetermined force being less than the first predetermined force;
wherein the proximal end of the basket is configured to fail when a third predetermined force is applied to the basket, the third predetermined force being greater than the second predetermined force.

20. A medical device, comprising:
a sheath comprising a proximal end and a distal end;
a handle at the proximal end of the sheath; and
a basket having a collapsed position when the basket is within the sheath and collapsed and an expanded position when the basket is positioned beyond the distal end of the sheath and expanded, the basket comprising a plurality of wires, a proximal end, and a distal end where the distal ends of the plurality of wires are joined, the distal ends of the plurality of wires releasing from each other when a predetermined force applied to the basket is less than both a force required to cause one of the plurality of wires to fail and a force required to cause the proximal end of the basket to fail, wherein the basket distal end comprises an over-molding joint;
wherein the basket distal end comprises a tip member, and the tip member releases from the plurality of wires when the joint fails.

21. A medical device, comprising:
a sheath comprising a proximal end and a distal end;
a handle at the proximal end of the sheath; and
a basket having a collapsed position when the basket is within the sheath and collapsed and an expanded position when the basket is positioned beyond the distal end of the sheath and expanded, the basket comprising a plurality of wires, a proximal end, and a distal end where the distal ends of the plurality of wires are joined at a joint, the distal ends of the plurality of wires releasing from each other when a predetermined force applied to the basket is less than both a force required to cause one of the plurality of wires to fail and a force required to cause the proximal end of the basket to fail, wherein at least one wire comprises stainless steel;

wherein the basket distal end comprises a tip member, and the tip member releases from the plurality of wires when the joint fails.

\* \* \* \* \*

UNITED STATES PATENT AND TRADEMARK OFFICE
CERTIFICATE OF CORRECTION

| | | |
|---|---|---|
| PATENT NO. | : 7,645,283 B2 | Page 1 of 1 |
| APPLICATION NO. | : 10/720598 | |
| DATED | : January 12, 2010 | |
| INVENTOR(S) | : Reynolds et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1286 days.

Signed and Sealed this

Sixteenth Day of November, 2010

David J. Kappos
*Director of the United States Patent and Trademark Office*